United States Patent [19]

Schlecker et al.

[11] Patent Number: 5,153,228
[45] Date of Patent: Oct. 6, 1992

[54] 9-AMINO-2-PHENYLBICYCLO(3.3.1)NO-NANES AND 9-AMINO-2-PHENYLBICYCLO(3.3.1)NON-2-ENES AND DRUGS CONTAINING THEM

[75] Inventors: Rainer Schlecker, Bissersheim; Hans P. Hofmann, Limburgerhof; Laszlo Szabo, Heidelberg, all of Fed. Rep. of Germany

[73] Assignee: BASF Aktiengesellschaft, Ludwigshafen, Fed. Rep. of Germany

[21] Appl. No.: 713,276

[22] Filed: Jun. 11, 1991

[30] Foreign Application Priority Data

Jun. 21, 1990 [DE] Fed. Rep. of Germany ....... 4019782

[51] Int. Cl.$^5$ ................. A61K 31/445; A61K 31/135; C07C 211/00; C07D 211/26
[52] U.S. Cl. ...................................... 514/647; 514/83; 514/240; 514/212; 514/319; 514/408; 540/450; 540/484; 540/611; 548/400; 548/577; 548/950; 546/205; 564/308
[58] Field of Search ................. 564/308; 514/647, 319; 546/205

[56] References Cited

U.S. PATENT DOCUMENTS

3,164,601 1/1965 Thesing et al. ..................... 564/308
3,742,055 6/1973 Freedman .......................... 564/308

FOREIGN PATENT DOCUMENTS

0246488 12/1962 Australia .......................... 564/308
0008163 2/1980 European Pat. Off. .
2619617 11/1976 Fed. Rep. of Germany .

OTHER PUBLICATIONS

Journal of the American Chemical Society, vol. 72, No. 8, Aug. 15, 1950, pp. 3405–3410, A. C. Cope, et al., "Cyclic Polyolefins. X. Synthesis of Phenylcycloocta-1,3-diene$^1$".
Journal of the Chemical Society, vol. 16, 1968, pp. 2032–2039, R. A. Appleton, et al., "Studies on Bicyclononanes. Part V.1 Formation of Substituted Bicyclononanes from Enamines".
Journal of the American Chemical Society, vol. 96, No. 1, Jan. 9, 1974, pp. 149–154, H. Caldararu, et al., "Electron Spin Resonance Study of Some Iminoxy Radicals. Stereochemistry of Bicyclic Systems".

Primary Examiner—Richard L. Raymond
Assistant Examiner—Peter G. O'Sullivan
Attorney, Agent, or Firm—Oblon, Spivak, McClelland, Maier & Neustadt

[57] ABSTRACT

9-Amino-2-phenylbicyclo-[3.3.1]nonanes and 9-amino-2-phenylbicyclo[3.3.1]non-2-enes of the formula I

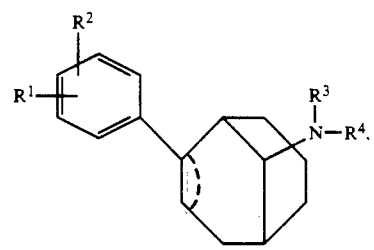

where $R^1$ and $R^2$ are identical or different and each is hydrogen, halogen, alkyl, alkoxy, dialkylamino, trifluoromethyl, hydroxyl, alkylthio, alkylsulfonyl or nitro, $R^3$ and $R^4$ are identical or different and each is hydrogen, alkyl or 1 to 5 or alkenyl or alkynyl of 2 to 5 carbon atoms, or benzyl, it also being possible for $R^3$ and $R^4$ together to form a saturated chain which contains from three to seven carbon atoms and can be substituted by phenyl, and where is a single or double bond, are used for producing drugs which act, in particular, on the central nervous system.

10 Claims, No Drawings

9-AMINO-2-PHENYLBICYCLO(3.3.1)NONANES AND 9-AMINO-2-PHENYLBICYCLO(3.3.1)NON-2-ENES AND DRUGS CONTAINING THEM

The present invention relates to 9-amino-2-phenylbicyclo[3.3.1]nonanes and 9-amino-2-phenylbicyclo[3.3.1]non-2-enes and drugs containing them.

It is an object of the present invention to develop novel drugs for the treatment of, in particular, disorders of the central nervous system.

We have found that this object is achieved by 9-amino-2-phenylbicyclo[3.3.1]nonanes and 9-amino-2-phenylbicyclo[3.3.1]non-2-enes of the formula I

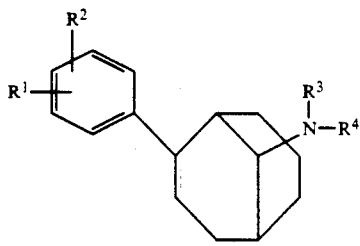

I where $R^1$ and $R^2$ are identical or different and each is hydrogen, halogen, alkyl, alkoxy, dialkylamino, trifluoromethyl, hydroxyl, alkylthio, alkylsulfonyl or nitro, $R^3$ and $R^4$ are identical or different and each is hydrogen, alkyl of 1 to 5 or alkenyl or alkynyl of 2 to 5 carbon atoms, or benzyl, it also being possible for $R^3$ and $R^4$ together to form a saturated chain which contains from three to seven carbon atoms and can be substituted by phenyl, and where is a single or double bond, which have valuable pharmacological properties, especially in their action on the central nervous system.

The compounds of the formula I can be prepared by reductive amination of the ketones II.

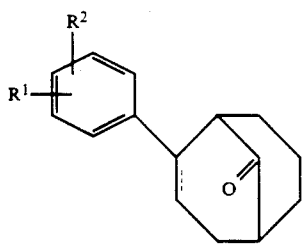

II

In this formula the symbols $R^1$ and $R^2$ and have the same meaning as in formula I. The processes for reductive amination of ketones are generally known and described, for example, in Houben-Weyl, Methoden der organischen Chemie, Volume 4/1d, 355–364 and 4/1c, 427–457. The reduction can be carried out using complex metal hydrides such as $NaBH_4$ or $NaBH_3CN$ or by catalytic hydrogenation in the presence of an amine $NHR^3R^4$. The ketones II are prepared by processes known from the literature (endo-II: saturated and with double bond: A. C. Cope et al., JACS 72 (1950) 3405–3410; exo-II saturated and with double bond: R. A. Appleton et al., J. Chem. Soc. (C), 1968, 2032–2039).

As a rule, the compounds according to the invention are mixtures of stereoisomers. However, the claim covers both the isolated exo- and endo-phenyl isomers Ia and Ib and the stereoisomers thereof.

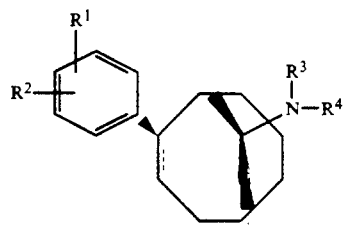

Ia

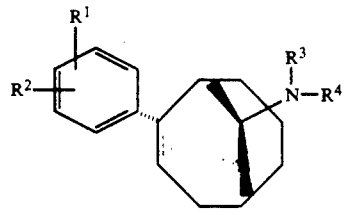

Ib

The compounds Ia and Ib according to the invention in turn are each a mixture of diastereomers which can be separated by chromatography or recrystallization. The pure diastereomers can be fractionated into the enantiomers by conventional methods, for example by conversion into diastereomeric salts of optically active acids such as dibenzoyltartaric acid, ditoluyltartaric acid or camphor-10-sulfonic acid and separation thereof by crystallization. The enantiomers can also be separated by chromatography on chiral phases.

The resulting compounds according to the invention can be converted into their salts with physiologically tolerated acids where appropriate. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid and benzoic acid. Others can be found in Fortschritte der Arzneimittelforschung, Vol. 10, 224 et seq., Birkhäuser Verlag, Basel and Stuttgart, 1966.

The acid addition salts are usually prepared in a conventional manner by mixing the free base or solutions thereof with the appropriate acid or solutions thereof in an organic solvent, for example a low alcohol such as methanol, ethanol or propanol, an ether such as methyl t-butyl ether, a ketone such as acetone or methyl ethyl ketone, or an ester such as ethyl acetate. It is also possible to use mixtures of the said solvents to improve crystallization. In addition, pharmaceutically acceptable aqueous solutions of acid addition salts of the compounds I according to the invention can be prepared by dissolving the free bases in an aqueous acid.

The compounds according to the invention are suitable for controlling diseases, especially for treating disorders of the central nervous system. They can be administered orally or parenterally (subcutaneously, intravenously, intramuscularly, intraperitoneally) in a conventional manner. Administration can also take place with vapors or sprays through the nasopharyngeal space.

The dosage depends on the age, condition and weight of the patient and on the mode of administration. As a rule, the daily dose of active substance is from about 10 to 1,000 mg per patient and day on oral administration and from about 1 to 500 mg per patient and day on parenteral administration.

The novel compounds can be used in the conventional solid or liquid pharmaceutical forms, e.g. uncoated or (film-)coated tablets, capsules, powders, granules, suppositories, solutions or sprays. These are produced in a conventional manner. The active substances can for this purpose be mixed with the conventional pharmaceutical auxiliaries such as tablet binders, fillers, preservatives, tablet disintegrants, flow regulators, plasticizers, wetting agents, dispersants, emulsifiers, solvents, retardants, antioxidants and/or propellant gases (cf. H. Sucker et al.: Pharmazeutische Technologie, Thieme-Verlag, Stuttgart, 1978). The resulting forms normally contain from 1 to 99% by weight of the active substance.

EXAMPLE 1

9-Amino-2-endo(4-methoxyphenyl)bicyclo[3.3.1]nonane

A solution of 1.0 g of NaBH$_3$CN in a little methanol is added dropwise to 5.1 g of 2-endo(4-methoxyphenyl)-bicyclo[3.3.1]nonan-9-one and 19.4 g of ammonium acetate in 60 ml of abs. methanol while cooling in ice. The mixture is left to stir overnight, the solvent is distilled out, and ice is added to the residue. The mixture is adjusted to pH 1 with 1N HCl, extracted with ether and made alkaline with 1N NaOH. The aqueous phase is extracted with ether, and the organic phase is separated off and dried. Dropwise addition of ethereal HCl results in 4.0 g of 9-amino-2-endo(4-methoxyphenyl)bicyclo[3.3.1]nonane hydrochloride, melting point 232° C.

EXAMPLE 2

9-Allylamino-2-endo(4-methylphenyl)bicyclo[3.3.1]nonane

A solution of 1.0 g of NaBH$_3$CN in a little methanol is added dropwise to 4.8 g of 2-endo(4-methylphenyl)-bicyclo[3.3.1]nonan-9-one and 22.1 g of allylammonium acetate in 50 ml of abs. methanol. The mixture is stirred overnight and then worked up as described in Example 1. 4.3 g of 9-allylamino-2-endo(4-methylphenyl(bicyclo-[3.3.1]nonane hydrochloride are obtained of melting point 202° C.

The following compounds according to the invention, inter alia, were prepared in a similar manner starting from the appropriate ketones.

TABLE

| Example | R$^1$ | R$^2$ | NR$^3$, R$^4$ | exo/endo | a) | M.p. (hydrochloride) |
|---|---|---|---|---|---|---|
| 3 | 4-OCH$_3$ | H | NH$_2$ | endo | \| | 120–123$^{b)}$ |
| 4 | H | H | NH$_2$ | endo | \| | 229–231 |
| 5 | H | H | N(CH$_3$)$_2$ | — | \|\| | 244–245 |
| 6 | H | H | NHCH$_3$ | — | \|\| | 218–221 |
| 7 | H | H | NHCH$_3$ | endo | \| | 255–258 |
| 8 | H | H | NHC$_2$H$_5$ | endo | \| | 227–230 |
| 9 | H | H | NH-CH$_2$CH=CH$_2$ | endo | \| | 189–191 |
| 10 | H | H | NH—C$_3$H$_7$n | endo | \| | 221–224 |
| 11 | H | H | N(CH$_3$)$_2$ | endo | \| | 231–234 |
| 12 | H | H | NH—C$_3$H$_7$ | — | \|\| | 248–251 |
| 13 | H | H | N-piperidinyl-phenyl | endo | \| | 277–280 |
| 14 | H | H | NH-CH$_2$C≡CH | exo | \| | 167–170 |
| 15 | H | H | NHC$_4$H$_9$ | exo | \| | 216–220 |
| 16 | H | H | NH-iPr | exo | \| | 223–225 |
| 17 | 4-Cl | H | NH-CH$_2$CH=CH$_2$ | — | \|\| | 203 |
| 18 | 4-Cl | H | NHCH$_3$ | — | \|\| | 249 |
| 19 | 4-Cl | H | NH$_2$ | — | \|\| | 247 |
| 20 | 4-F | H | NH-CH$_2$CH=CH$_2$ | — | \|\| | 216–218 |
| 21 | 4-F | H | NHCH$_3$ | — | \|\| | 224 |
| 22 | 4-F | H | NH$_2$ | — | \|\| | 238–239 |
| 23 | 4-CH$_3$ | H | NH-CH$_2$CH=CH$_2$ | — | \|\| | 213–215 |
| 24 | 4-CH$_3$ | H | NHCH$_3$ | — | \|\| | 240 |
| 25 | 4-CH$_3$ | H | NH$_2$ | — | \|\| | 239 |
| 26 | 4-OCH$_3$ | H | NH-CH$_2$CH=CH$_2$ | — | \|\| | 219 |

TABLE-continued

| Example | R¹ | R² | NR³, R⁴ | exo/endo | a) | M.p. (hydrochloride) |
|---|---|---|---|---|---|---|
| 27 | 4-OCH₃ | H | NHCH₃ | — | ‖ | 198 |
| 28 | 4-OCH₃ | H | NH₂ | — | ‖ | 223-224 |
| 29 | H | H | NH₂ | — | ‖ | 258 |
| 30 | 4-F | H | NH-CH₂-CH=CH₂ | endo | \| | 222 |
| 31 | 4-F | H | NHCH₃ | endo | \| | 283 |
| 32 | 4-(CH₃)₃C— | H | NH-CH₂-CH=CH₂ | — | ‖ | 215 |
| 33 | 4-(CH₃)₃C— | H | NH₂ | — | ‖ | 273 |
| 34 | 4-(CH₃)₃C— | H | NHCH₃ | — | ‖ | 309 |
| 35 | 4-(CH₃)₃C— | H | NH-CH₂-CH=CH₂ | endo | \| | 227 |
| 36 | 4-(CHJ₃)₃— | H | NH₂ | endo | \| | 256 |
| 37 | 4-(CH₃)₃C— | H | NHCH₃ | endo | \| | 351 |
| 38 | 4-Cl | 3-Cl | NH-CH₂-CH=CH₂ | — | ‖ | 215 |
| 39 | 4-Cl | 3-Cl | NH₂ | — | ‖ | 236 |
| 40 | 4-Cl | 3-Cl | NHCH₃ | — | ‖ | 261 |
| 41 | 4-OCH₃ | H | NH-CH₂-CH=CH₂ | endo | \| | 156 |
| 42 | 4-OCH₃ | H | NHCH₃ | endo | \| | 263 |
| 43 | 4-CH₃ | H | NH-CH₂-CH=CH₂ | endo | \| | 202 |
| 44 | 4-CH₃ | H | NHCH₃ | endo | \| | 261-263 |
| 45 | 4-CH₃ | H | NH₂ | endo | \| | 251 |
| 46 | 4-OCH₃ | H | NH₂ | endo | \| | 232 |
| 47 | 4-Cl | 3-Cl | NHCH₃ | endo | \| | 277 |
| 48 | 4-Cl | 3-Cl | NH-CH₂-CH=CH₂ | endo | \| | 171 |
| 49 | 4-Cl | 3-Cl | NH₂ | endo | \| | 256 |
| 50 | 4-Cl | H | NH₂ | endo | \| | 249 |
| 51 | 4-Cl | H | NH-CH₂-CH=CH₂ | endo | \| | 200 |
| 52 | 4-Cl | H | NH₂ | endo | \| | 262 |
| 53 | 4-Cl | H | NHCH₃ | endo | \| | 292 | a) ‖ = double bond. \| = single bond
b) free base

EXAMPLE 54

Separation of 9-amino-2-endo-phenylbicyclo[3.3.1]nonane diastereomers 50 g of product from Example 4 are recrystallized from water three times. 15 g of 9-syn-amino-2-endo-phenylbicyclo[3.3.1]nonane are obtained of melting point 210°-212° C.

The aqueous mother liquors are combined, made alkaline with 1N NaOH, and etheral HCl is added. The crystal are filtered off with suction and recrystallized from isopropanol three times. 3 g of 9-anti-amino-2-endophenylbicyclo[3.3.1]nonane are obtained of melting point 278° C. The assignment of the relative configurations was based on the ¹³C-NMR spectra of the substances.

We claim:

1. A 9-amino-2-phenylbicyclo[3.3.1]nonane or 9-amino-2-phenylbicyclo[3.3.1]non-2-ene of the formula I

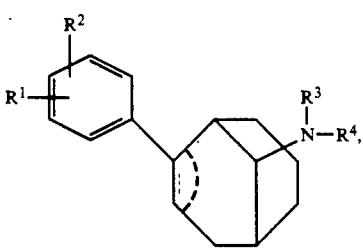

where R¹ and R² are identical or different and each is hydrogen, halogen, alkyl, alkoxy, dialkylamino, trifluoromethyl, hydroxyl, alkylthio, alkylsulfonyl or nitro, R³ and R⁴ are identical or different and each is hydrogen, alkyl of 1 to 5 or alkenyl or alkynyl of 2 to 5 carbon atoms, or benzyl, it also being possible for $R^3$ and $R^4$ together to form a saturated chain which contains from three to seven carbon atoms and can be substituted by phenyl, and where ― is a single or double bond.

2. A 9-amino-2-phenylbicyclo[3.3.1]nonane or 9-amino-2-phenylbicyclo[3.3.1]non-2-ene of the formula I as claimed in claim 1, where $R^1$ and $R^2$ are each, independently of one another, hydrogen, fluorine, chlorine, $C_1$-$C_4$-alkyl or methoxy, $R^3$ and $R^4$ are each, independently of one another, hydrogen, $C_1$-$C_4$-alkyl, allyl or propargyl, or $R^3$ and $R^4$ together form a saturated chain which contains 4 or 5 carbon atoms and can be substituted by phenyl.

3. A drug for oral use which, besides conventional pharmaceutical auxiliaries, contains 10 to 1,000 mg per dose of a compound of the formula I as claimed in claim 1 as active substance.

4. A drug for parenteral use which, besides conventional pharmaceutical auxiliaries, contains 1 to 500 mg per dose of a compound of the formula I as claimed in claim 1 as active substance.

5. A 9-amino-2-phenylbicyclo[3.3.1]nonane of the formula I

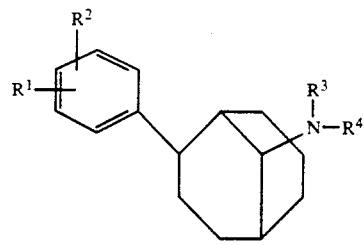

where
$R^1$ and $R^2$ are identical or different and each is hydrogen, halogen, alkyl or alkoxy,
$R^3$ and $R^4$ are identical or different and each is hydrogen, alkyl of 1 to 5 or alkynyl of 2 to 5 carbon atoms, or benzyl,
or $R^3$ and $R^4$ together form a saturated chain which contains from 3 to 7 carbon atoms and can be substituted by phenyl.

6. The 9-amino-2-phenylbicyclo[3.3.1]nonane of the formula I as claimed in claim 5, wherein $R^1$, $R^2$, $R^3$ and $R^4$ each is hydrogen.

7. A drug for oral use which, besides conventional pharmaceutical auxiliaries, contains 10 to 1,000 mg per dose of a compound of the formula I as claimed in claim 5 as active substance.

8. A drug for parenteral use which, besides conventional pharmaceutical auxiliaries, contains 1 to 500 mg per dose of a compound of the formula I as claimed in claim 5 as active substance.

9. A drug for oral use which, besides conventional pharmaceutical auxiliaries, contains 10 to 1,000 mg per dose of a compound of the formula I as claimed in claim 6 as active substance.

10. A drug for parenteral use which, besides conventional pharmaceutical auxiliaries, contains 1 to 500 mg per dose of a compound of the formula I as claimed in claim 6 as active substance.

* * * * *